US007669488B2

(12) United States Patent
Bridge et al.

(10) Patent No.: US 7,669,488 B2
(45) Date of Patent: Mar. 2, 2010

(54) IMPACTOR AUTOMATION

(75) Inventors: Michael James Bridge, Cheshire (GB); Dominic Ewan Harvey, Cheshire (GB); Christopher Ian Hansford, Cheshire (GB)

(73) Assignee: Astech Projects Limited, Runcorn, Cheshire (GB)

( * ) Notice: Subject to any disclaimer, the term of this patent is extended or adjusted under 35 U.S.C. 154(b) by 80 days.

(21) Appl. No.: 11/621,933

(22) Filed: Jan. 10, 2007

(65) Prior Publication Data

US 2008/0047372 A1    Feb. 28, 2008

(30) Foreign Application Priority Data

Aug. 24, 2006   (GB)   ................................. 0616799.5

(51) Int. Cl.
*G01N 1/22*    (2006.01)
(52) U.S. Cl. .................................................. 73/863.22
(58) Field of Classification Search .............. 73/863.22, 73/863.01; 422/62, 68.1; 436/43, 47; 209/133, 209/138; 118/71, 676, 677, 679; 401/16
See application file for complete search history.

(56) References Cited

U.S. PATENT DOCUMENTS

| 6,712,285 | B2 * | 3/2004 | Provenaz et al. ................ 239/1 |
| 6,723,568 | B1 * | 4/2004 | Liu et al. ..................... 436/174 |
| 6,915,714 | B2 * | 7/2005 | Sanderson et al. ........ 73/863.01 |
| 2004/0250634 | A1 * | 12/2004 | Liu et al. ................. 73/863.22 |
| 2005/0028616 | A1 * | 2/2005 | Marple et al. ............ 73/863.22 |

FOREIGN PATENT DOCUMENTS

WO  PCT/US2007/008924    10/2007
WO      WO 2007120700 A2 *  10/2007

* cited by examiner

*Primary Examiner*—Hezron Williams
*Assistant Examiner*—Tamiko D Bellamy
(74) *Attorney, Agent, or Firm*—Blakely, Sokoloff, Taylor & Zafman LLP

(57) ABSTRACT

The application describes an automated system for carrying out tests using a cascade impactor 10 of the type having multiple impactor stages each comprising a respective stage body 30, the stage bodies being shaped to enable them to be assembled in a stack in which they locate one upon another. The system includes an expander device 90 having respective arms for supporting each of the stage bodies, and a mechanism for separating the arms along the axial direction to disassemble the impactor 10.

40 Claims, 15 Drawing Sheets

(PRIOR ART)

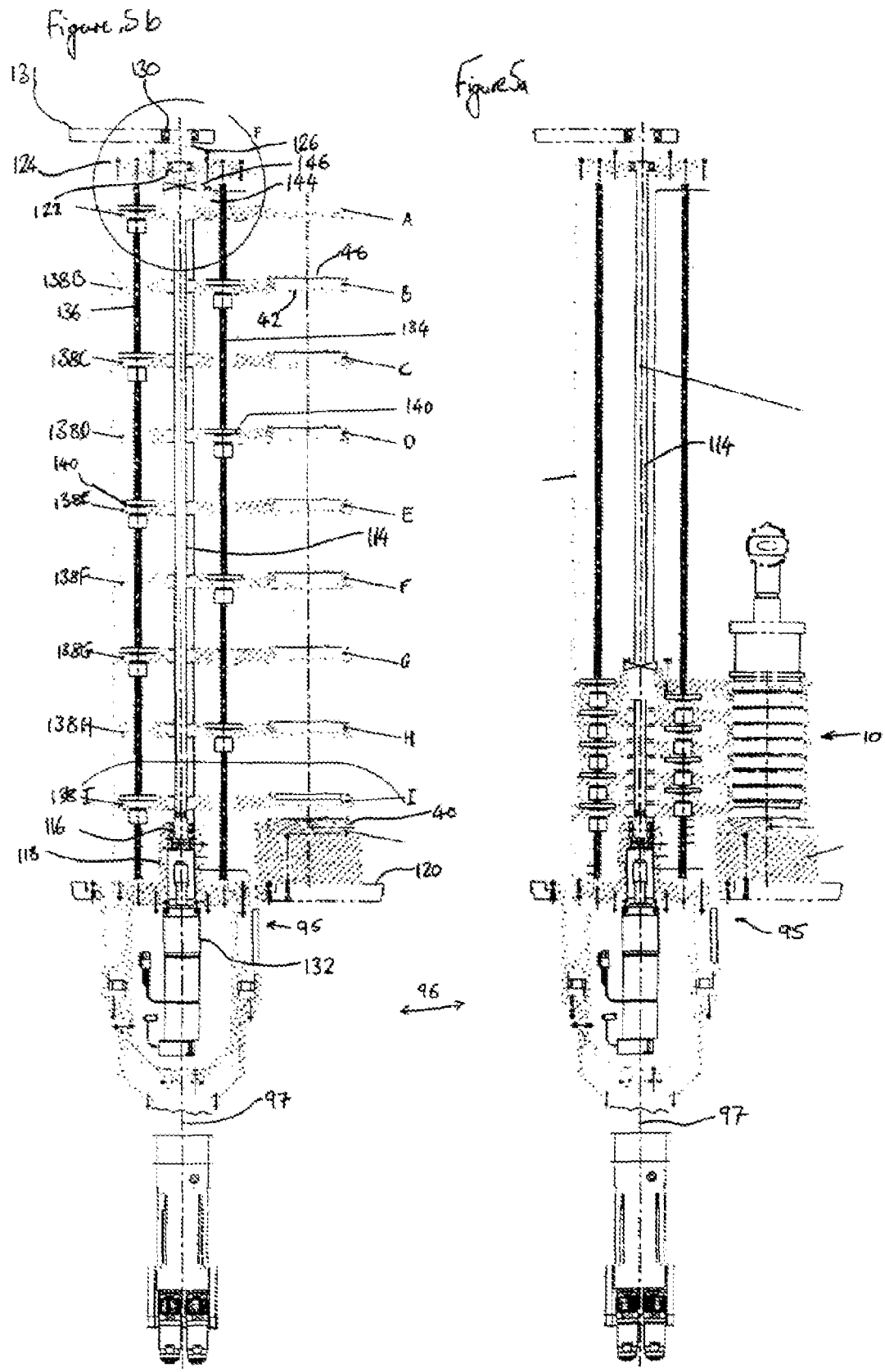

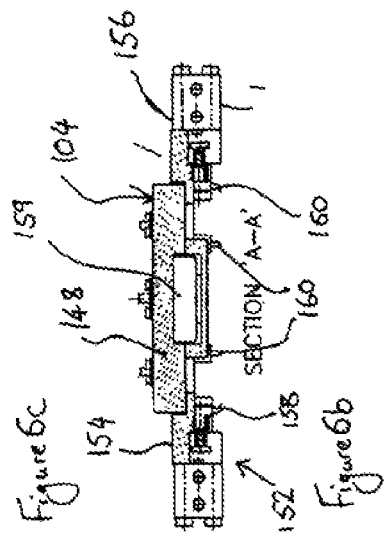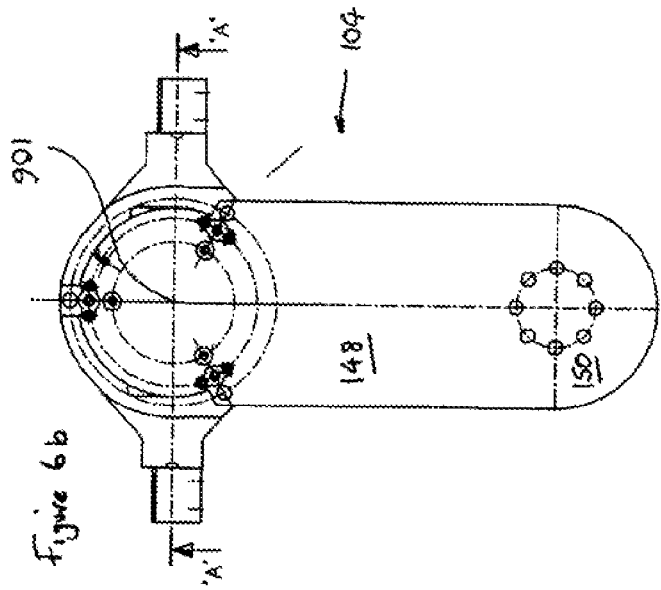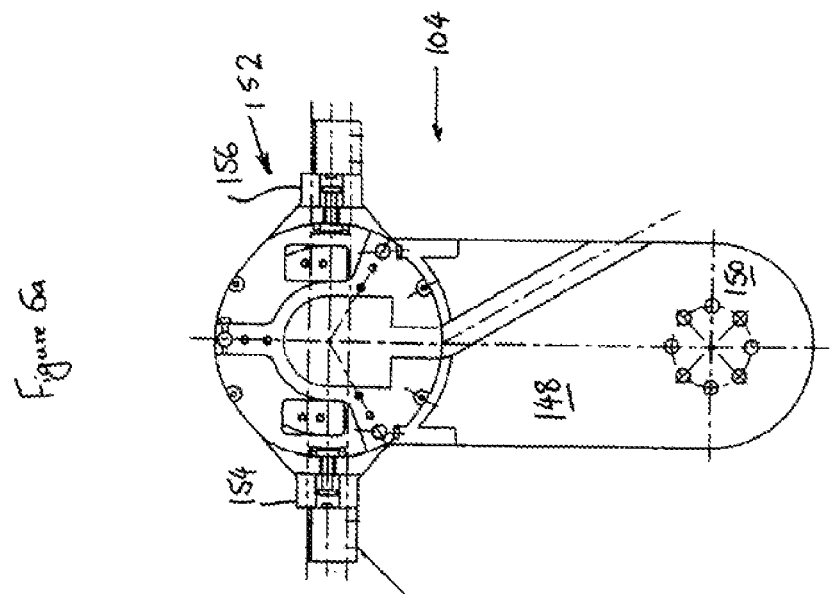

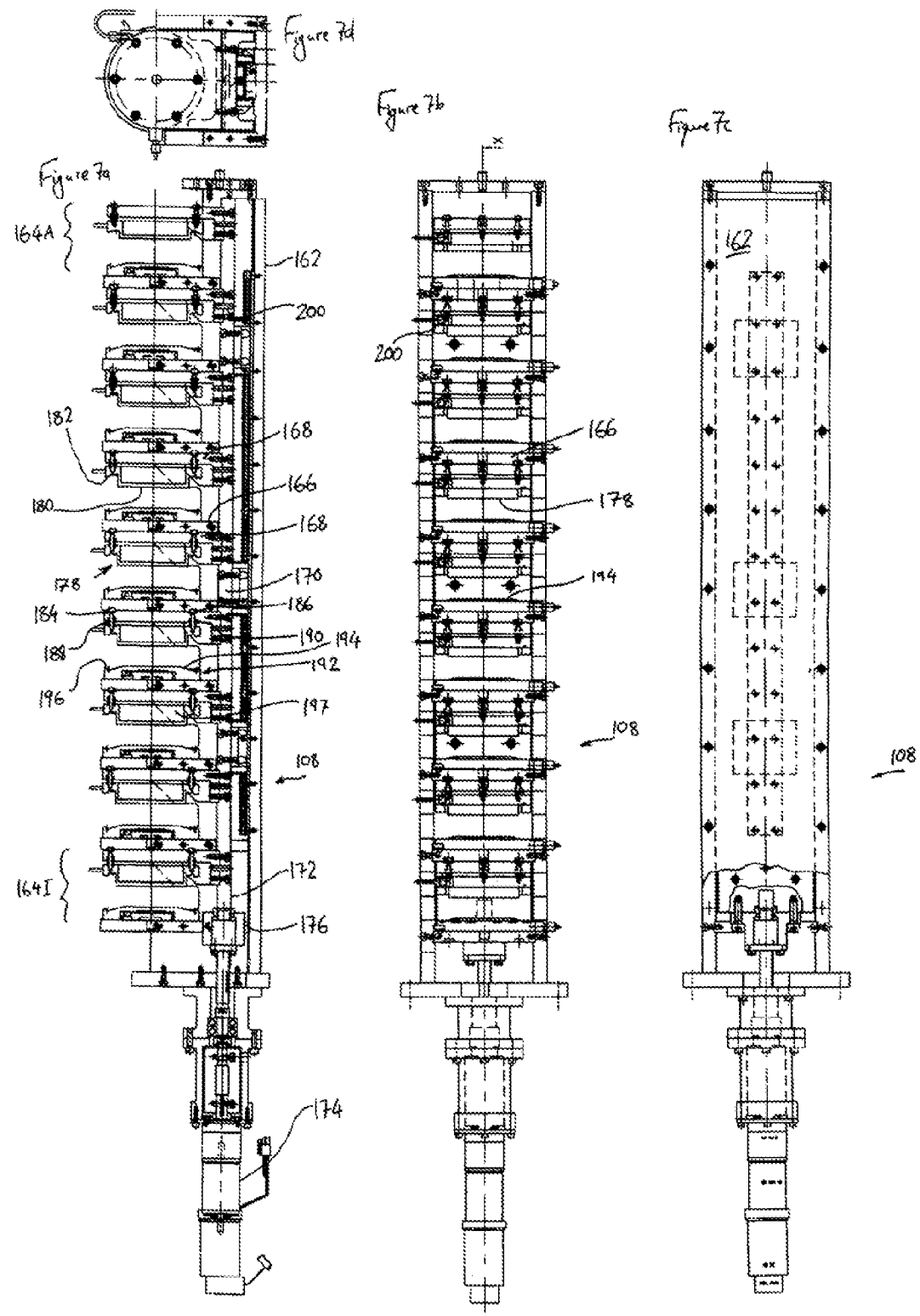

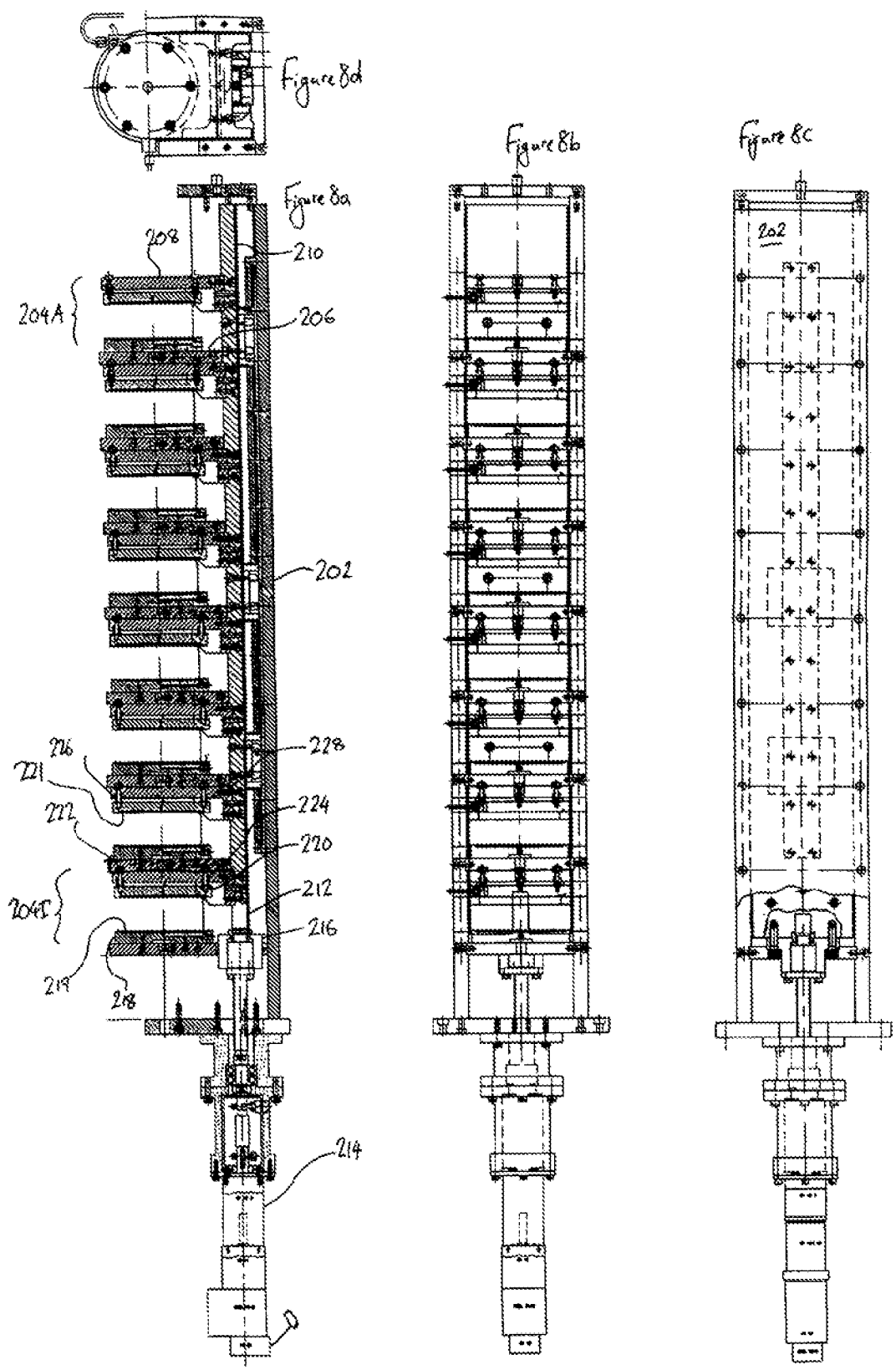

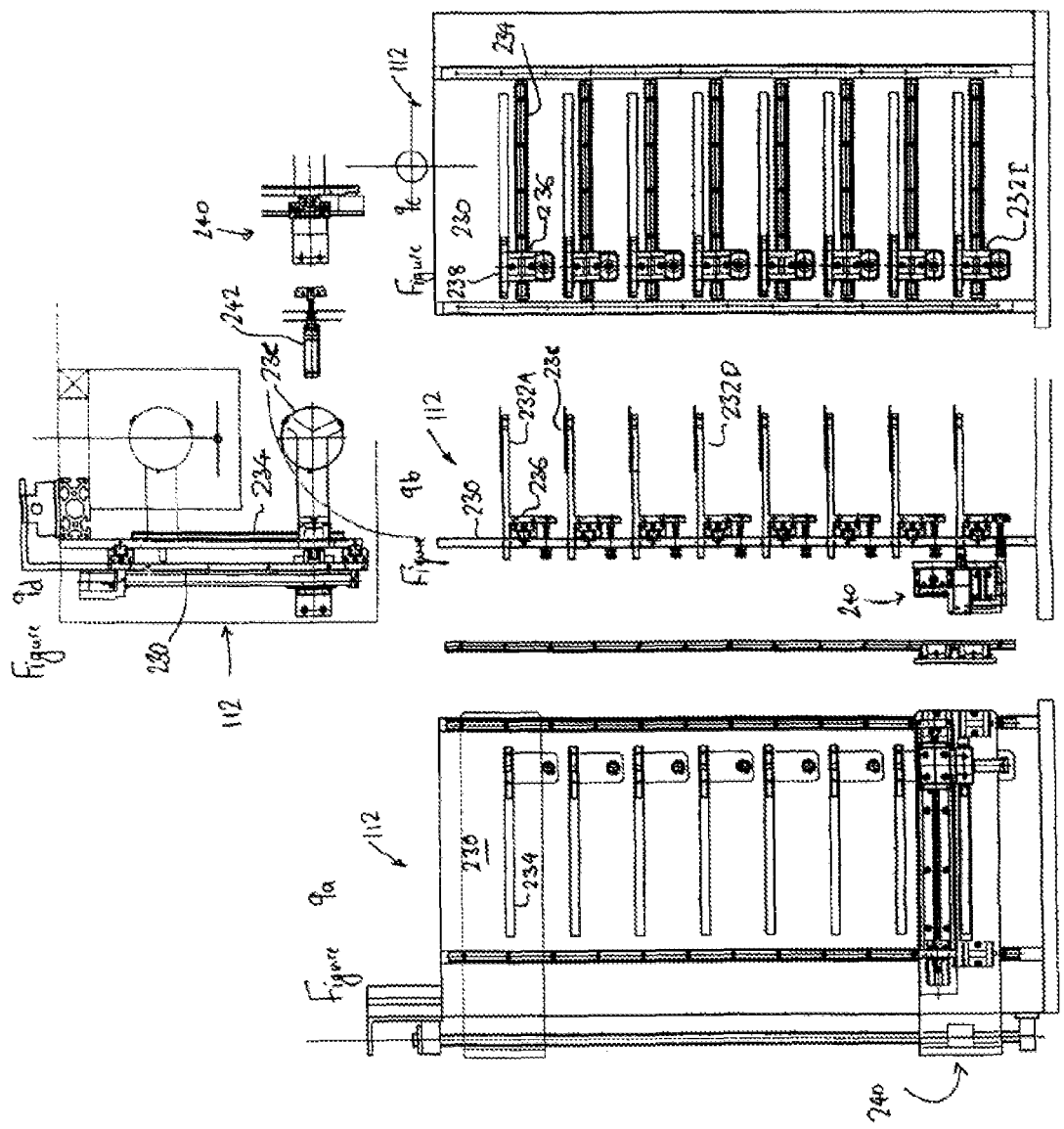

Figure 14
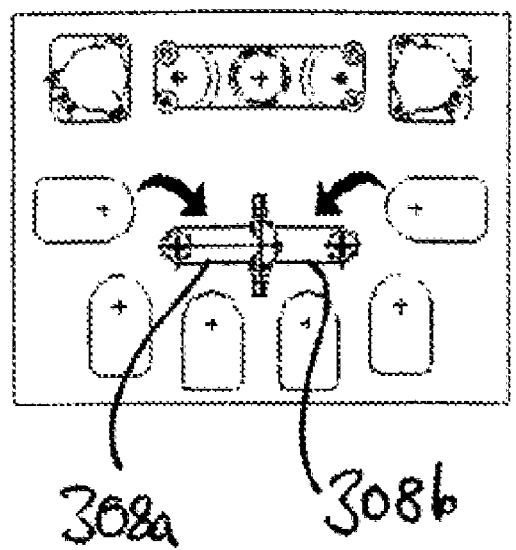
308a  308b
302a  302b
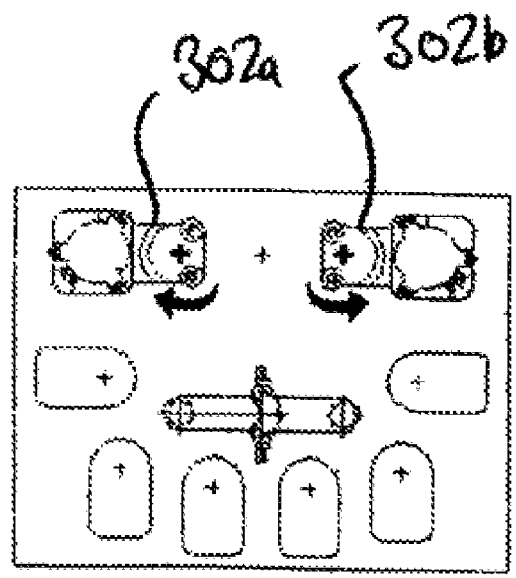
Figure 15

300

IMPACTOR AUTOMATION

CROSS-REFERENCE TO RELATED APPLICATIONS

The present patent application claims priority from United Kingdom Patent Application No, 0616779.5, filed on Aug. 24, 2006.

BACKGROUND OF THE INVENTION

1). Field of the Invention

The present invention is concerned with automation of tests carried out using a cascade impactor.

2). Discussion of Related Art

Cascade impactors are in themselves well known. They are used to analyze particle size distribution in aerosols. A particularly important application is in the testing of inhalers—devices used to dispense a controlled pharmaceutical dose into the mouth and lungs of a patient. Inhalers are used to treat asthma and other conditions. The pharmaceutical drug is typically in powdered or liquid form, much of its bulk being made up of a carrier and only a small percentage by the active ingredient. In use the patient releases a controlled dose of the powder or liquid using a mechanical arrangement such as a trigger lever. The patient, then draws it into the lungs by sucking. Penetration of the drug—and hence of the active ingredient itself—into the lungs is affected by particle size, so during manufacture it is necessary to verify, by testing of sample inhalers, that a suitable particle size distribution is being achieved. The cascade impactor is used for this purpose.

SUMMARY OF THE INVENTION

A widely used type of impactor, known in the trade as the Andersen impactor, is illustrated in FIG. 1 and will be described below. It comprises multiple separable stages which locate one upon another to form, a cylindrical conduit through which a test sample is drawn. The sample is supplied to an impactor inlet, formed e.g. as a mouthpiece, at one end of the conduit formed by the stages, and a partial vacuum is applied to the other end to draw through the impactor an aerosol containing the sample. The internal formation of the impactor causes material with successively diminishing particle size to collect in the impactor stages. This material is then recovered from the internal surfaces of the cascade impactor.

This has typically been a manual process involving disassembly of the impactor and then rinsing of each component with solvent. The solvent/sample resulting from rinsing of each component is separately collected for analysis. The manual process is labour intensive.

There have been previous attempts to automate sample recovery with an Andersen type impactor, but these have suffered from shortcomings. U.S. Pat. No. 6,915,714 (Sanderson et al) describes one such system, which uses upper and lower clamping plates, coupled in clam shell fashion, to define a set of chambers arranged side-by-side in which the impactor components are placed. Recovery of the sample material is by circulation of solvent through the chambers. The process of disassembling the impactor is not considered.

According to a first aspect of the present invention, there is an expander device for expanding a cascade impactor of the type comprising multiple impactor stages each comprising a respective stage body, the stage bodies being shaped to enable them to be assembled in a stack, one locating upon another, to form a conduit for through-flow of an aerosol sample, the slack having an axis, the expander device comprising a respective arm member for supporting each stage body, an arrangement for supporting the arm members such that they are movable along the direction of the said axis, and a mechanism for moving the arm members away from each other along the direction of the said axis to expand the impactor stages, and for moving them together along the direction of the said axis to re-assemble the impactor stages.

By expanding the impactor in this way, its component parts (such as plates) are each made available for concurrent processing in subsequent steps. The impactor stages may in fact be secured to or even integral with the arm members and conveyed to processing stations in/by them. The reference to an axis of the impactor does not necessarily imply that it is cylindrical, merely that it has a long dimension which is the direction of the axis, but typically it is in fact cylindrical.

Preferably the arm members are slidably supported on at least one elongate guide member extending in the direction of the said axis. They may be driven by means of a lead screw, a rotary lead screw drive, and at least one traveller which engages the lead screw so as to be moved along the lead screw by rotation of it.

In a preferred embodiment, the expander device is adapted to receive the impactor with its axis at least substantially upright, at least some of the arm members having an extensible coupling to their neighbouring arm member, the extensible coupling being constructed to accommodate some relative motion of the neighbouring arm members but to prevent them from moving apart more than a maximum distance, so that raising the top-most arm member causes arm members beneath it to be suspended from it through the extensible couplings, and thereby to be separated from each other. The extensible coupling may for example comprise an elongate coupling member which is coupled to one arm member and is movably received by the other, the elongate coupling member having a slop feature which limits its movement relative to the said other arm member to define the said maximum distance. The elongate coupling member is preferably a pin with an enlarged head received in a bore in the said other arm member.

The impactor stages are to be conveyed from one processing station to another, and in a preferred embodiment this is achieved by mounting the expander device for rotation about the said axis, or about an axis substantially parallel to the said axis, the stage bodies being offset from the rotational axis so that by rotary movement of the device the stage bodies are movable from one processing station to another.

Firing of a device being tested may be carried out whilst the impactor is carried in the expander device. To this end, a preferred embodiment further comprises a support platform for supporting the assembled impactor from beneath, the support platform being provided with a conduit connectable to a vacuum source to cause the aerosol to be drawn through the impactor.

After the cascade impactor is expanded, recovery of sample material from it can be carried out.

In accordance with a second aspect of the present invention, there is a recovery device for recovering material collected upon working surfaces of components of a cascade impactor of the type comprising multiple impactor stages each comprising a respective stage body, the stage bodies being shaped to enable them to be assembled in a stack, locating one upon another, to form a conduit for through-flow of an aerosol sample, the stack having an axis, and the recovery device comprising multiple recovery stages separated vertically one from another and each adapted to receive a component from a respective impactor stage, each station comprising relatively movable upper and lower receptacle parts each shaped to receive the impactor component between themselves aid having peripheral sealing surfaces, the device further comprising a drive mechanism for moving the upper and lower parts apart, so that the impactor components are able to be introduced between them along a lateral direction, and for subsequently moving the upper and lower receptacle parts together, causing the peripheral sealing surfaces to seat upon each other or upon the impactor parts, so that each recovery stage forms a closed recovery chamber containing its impactor part, the recovery device further comprising conduits for circulating liquid through each of the recovery chambers.

Due to its layout, the recovery device is able to receive and process multiple impactor components concurrently.

Some form of agitation is needed to cause the sample material to be collected in the liquid (typically this process is in feet dissolution of the material in a solvent) and to homogenize the mixture/solution. To this end, in a preferred embodiment, each recovery chamber is connectable to a closed loop incorporating a pump for recirculating liquid through the recovery chamber to promote dissolution in the liquid of material collected upon the said working surfaces. The device preferably further comprises means for dispensing a controlled dose of liquid into the closed loop.

The liquid containing the sample material must be collected. A preferred embodiment comprises a valve arrangement for diverting the liquid from the closed loop to a collection vessel.

Withdrawal of the liquid from the recovery chambers may be improved, in a preferred embodiment, by virtue of mounting of the recovery device on a power driven tilting platform to enable it to be inclined to cause liquid in the recovery chambers to flow toward fluid outlets from the recovery chambers.

Preferably at least one of the upper aid lower receptacle parts is spring mounted, so that when the upper and lower receptacle parts are brought together the spring mounting(s) bias them toward each other.

It is desirable to minimize the quantity of liquid used in recovery. In a preferred embodiment of the recovery device, for use with hollow cylindrical impactor stage bodies, at least one of the upper and lower receptacle members has a space saver projection surrounded by the peripheral sealing surface, the projection being insertable into the impactor stage body by the relative motion of the upper and lower receptacle parts.

In accordance with a third aspect of the present invention, there is a system for automatic recovery of test material from a cascade impactor of the type comprising multiple impactor stages each comprising a respective stage body, the stage bodies being shaped to enable them to be assembled in a stack, locating one upon another, to form a conduit for through-flow of an aerosol sample, the stack having an axis, and the system comprising an expander device for separating the impactor stages from one another along the axial direction and supporting them in the resulting expanded configuration, at least one recovery station having multiple recovery stages separated along the axial direction for receiving respective components of the impactor stages, means for concurrently moving multiple components of the expanded impactor stages to the recovery station.

The system allows for concurrent processing of multiple components, maximizing throughput.

Preferably the expander device is mounted for rotation and provided with a powered drive, enabling it to move the impactor stages along a circular path to and from a recovery station.

Individual components from a single impactor stage must sometimes he separately treated. A preferred embodiment of the present invention is for use with a cascade impactor of the type in which the impactor stages have respective impaction plates supportable upon respective impactor stage bodies, the aforementioned recovery station being a stage body recovery station for recovering material collected on the stage bodies and the system further comprising a plate recovery station and a plate handling device comprising multiple plate handling arms separated from each other along the axial direction, each plate handling arm having means for engaging a respective impaction plate, the plate handling device thus being adapted to engage multiple impaction plates and to move them concurrently to the plate recovery station. Preferably the plate handling arms are commonly mounted upon a rotary platform provided with a powered drive.

Some impactor applications require the impactor plates to be pre-coated e.g. with silicone. In a preferred embodiment, the system further comprises a plate coating station for applying a coating to the impaction plates. The plate coating station is preferably arranged to receive the plates from the plate handling device. In a preferred embodiment it comprises at least one spray head for spray coating the impaction plates. An alternative is to carry out coating by immersion of the plates.

It is preferable, although not necessarily essential, for the system to fire the dispensing device providing the sample (e.g. an inhaler) automatically into the cascade impactor. In a suitable embodiment the firing arrangement comprises an automated mechanical arrangement for presenting the dispensing device to a mouthpiece of the cascade impactor, a pump for providing a partial vacuum, and an arrangement of valves and conduits for connecting the pump to an outlet of the cascade impactor to cause air to be drawn through the impactor and the device. The system preferably further comprises an automated mechanism for actuating a trigger arrangement of the dispensing device, to release a pharmaceutical dose from it.

Preferably the system further comprises a store for multiple dispensing devices (e.g. inhalers), a movable platform for carrying a dispensing device, and an automated manipulation arrangement for collecting a dispensing device from the store and locating it at the platform. The store may comprise a carousel, with multiple device-receiving locations at intervals around its periphery, so that by rotating the carousel different device-receiving locations are made available to the automated manipulation arrangement.

Preferably, the system comprises a waste firing station for firing unwanted doses from the dispensing device, the said platform being arranged to move the device between the waste firing station and the firing arrangement.

Preferably the or each recovery station defines multiple recovery chambers and each recovery chamber is connectable to a closed fluid circuit comprising a fluid reservoir, a pumping device and one or more recovery chambers, enabling fluid to be circulated around the closed loop, via the reservoir and recovery chamber(s), to cause collected material to pass into the liquid and be homogenized. A controlled quantity of liquid may be supplied to the closed loop by means of a metered displacement type pump.

To facilitate withdrawal of liquid from the closed loop, the reservoir has an inlet and an outlet, the inlet being higher than the outlet and being above a level to which the reservoir is filled, and the pumping device and/or associated valves being controllable to circulate the liquid around the closed loop in a forward direction for material collection and homogenization, the liquid passing into the reservoir through the inlet and out through the outlet, and in a reverse direction for discharge of the liquid, causing liquid to be withdrawn from the outlet without being drawn in through the inlet.

In accordance with a fourth aspect of the invention there is a coating station for coating impaction plates of a cascade impactor, the coating station having multiple supports for receiving respective impaction plates, at least one spray heads and a drive arrangement for moving the supports relative to the head(s) to pass impaction plates carried upon the supports through spray from the head(s).

BRIEF DESCRIPTION OF THE DRAWINGS

Specific examples of the present invention will now he described, by way of example only, with reference to the accompanying drawings, in which:

FIGS. 5a and 5b are axial sections through an expander unit, used in the recovery subsystem, the two drawings showing this unit in two different configurations;

FIGS. 6a-6c are respectively a plan view from beneath, a plan view from above, and a sectional view along lines A-A of plate-handing arms used in the recovery subsystem;

FIGS. 7a-7d are respectively
(a) a longitudinal section,
(b) a front view,
(c) a rear view, and
(d) a plan view of a stage recovery device used in the recovery subsystem;

FIGS. 8a-8d are respectively
(a) a longitudinal section,
(b) a front view,
(c) a rear view, and
(d) a plan view of a plate recovery device used in the recovery subsystem;

FIGS. 9a-9d are respectively
(a) a rear view,
(b) a longitudinal section,
(c) a front view, and
(d) a plan view of a plate coating station used in the recovery subsystem;

FIGS. 10-19 are schematic representations, in plan, of a second form of recovery subsystem, showing the subsystem in different configurations to illustrate its mode of operation;

DETAILED DESCRIPTION OF THE INVENTION

Figure 1:
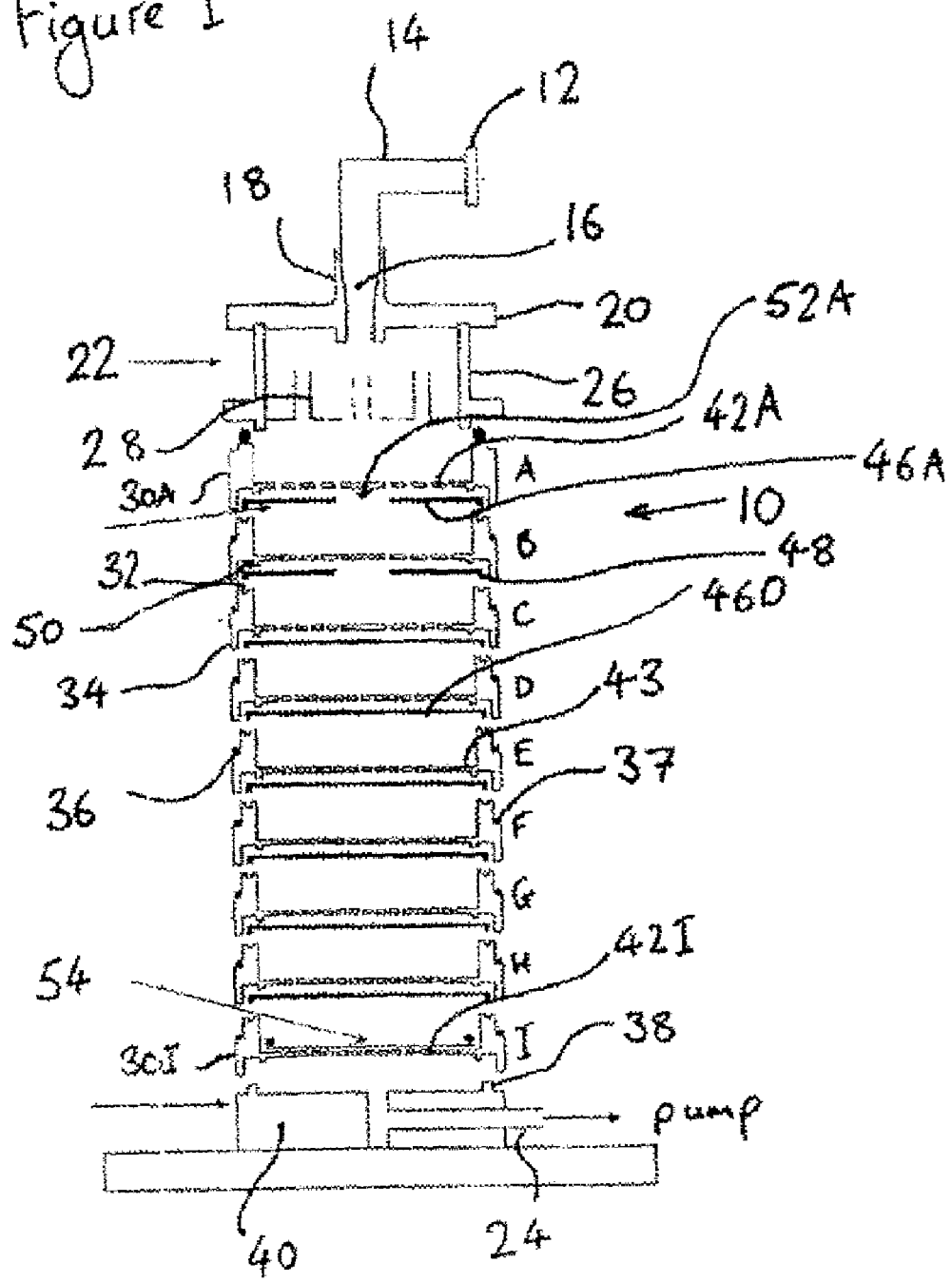
FIG. 1 is a somewhat stylized view, in axial section, of a known cascade impactor.

The cascade impactor 10 illustrated in FIG. 1 is of a well known and widely commercially available type known as an Andersen impactor. In use, a sample inhaler (omitted from this drawing) is presented to an elastomer (specifically rubber) mouthpiece 12 at the opening of a tubular throat 14, formed as an elbowed metal part with a frusto-conical taper 16 at its end remote from the mouthpiece, the taper forming a sealed friction fit in a complimentarily shaped inlet tube 18 of a lid 20 of a preseparator 22. Air is drawn through tire inhaler and tire impactor, via the throat, by means of a conduit 24 connected to a vacuum pump, which again is omitted from this drawing. The air passing through the impactor thus contains a dose of pharmaceutical from the inhaler.

The largest particles in the dose are typically bulking material such as lactose, and are collected in the preseparator 22. The preseparator comprises a cylindrical preseparator body 26 which receives the lid 20 and within which is supported a removable preseparator vessel 28 which is partially filled with a solvent. The preseparator vessel 28 is open toward the inlet tube 18. In use, air flows through the preseparator around the outside of the preseparator vessel 28, but the larger of the particles entrained in the air flow, due to their momentum, impinge upon and are collected in the liquid in the preseparator vessel 28.

Beneath the preseparator is a set of collection stages A-I, arranged one above (and hence upstream of) another, which serve to collect particles of progressively diminishing size. Each collection stage comprises:

1. An annular stage body 30A-I. The stage bodies rest one upon the next and together define, when assembled together, a tubular conduit through which air passes. Each is shaped to locate upon and seal against its neighbours, having at its base an annular cut-away which defines a shoulder 32 to rest upon the body below and a downwardly projecting locating wail 34. Upwardly facing shoulders 36 in the outer surface of each stage body 30 receive elastomeric "O" rings 37 which, when the collection stages of the impactor are suitably biased together, form seals against ingress of air. The bottom-most stage body 301 locates upon a circular projection 38 of a base plate 40.

2. A stage filter 42A-I supported on a ledge 43 within the respective stage body 30A-I. The stage filters are each formed by a circular, sintered metal plate with a large number of through-going apertures. From top to bottom of the impactor, the filters are progressively finer. That is, the apertures in the filters are progressively smaller and more numerous.

3. An impaction plate 46A-I formed as a circular metal plate with a downwardly turned outer lip 48. The lip of each impaction plate is supported in a circular recess 50 of the stage body beneath it.

Note that the path through each stage for airflow is somewhat convoluted, leading-through the stage filter 42 and around the outside of the impaction place 46, through the annular space between the impaction plate and the adjacent locating wail 34. The top two stages A and B also provide for air passage through a central aperture 52A,B in the impaction plate 46A,B and in these stages the portion of the filter above the aperture is continuous—i.e. it has no apertures. Due to their momenta, the particles in the airflow tend, after passing through the filter, to proceed onto the impaction plate and be collected there, rather than following the convoluted path taken by the air, and each impaction place collects successively smaller particles. The impaction plates 46A-I may he coated to improve adhesion and collection of the particles. A back-up filter 54 in the lowermost stage I prevents escape of the finest particles from the sample.

Material collected on the impaction plates 46, the filters 42, the interiors of the stage bodies 30 and in the throat 14 and the preseparator 22 needs to be recovered for analysis.

Figure 2:
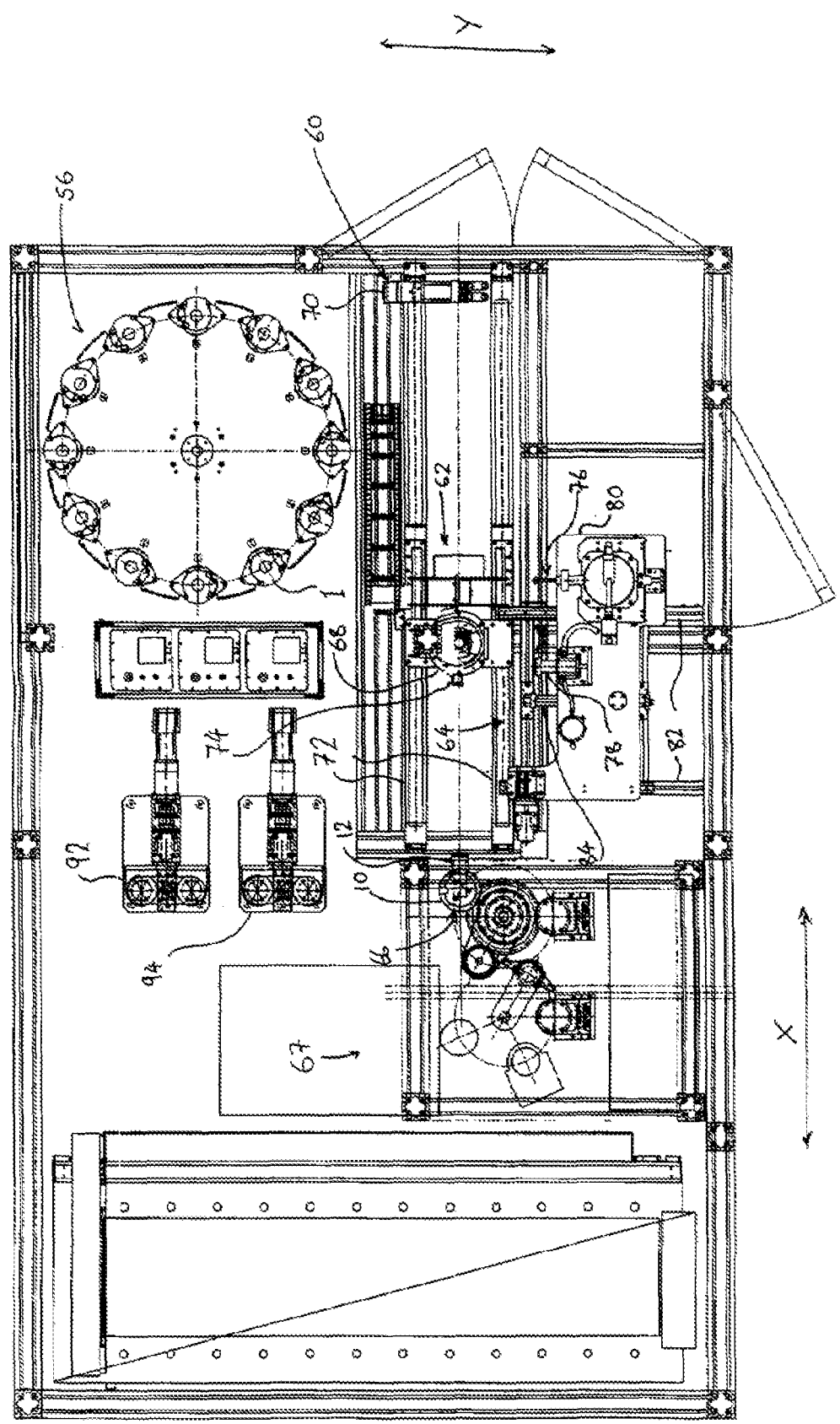
FIG. 2 is a plan view of a system embodying the present invention.

The system to be described below serves to automate the operation of the impactor and the recovery of the collected material from it. Very briefly summarized, with particular reference to FIG. 2, it comprises a carousel 56 for storing devices 1 to be tested, which in this embodiment are inhalers used for treatment of asthma. A device dispensing unit 60 is used to take the devices from the carousel to a device transfer unit 62. Each device contains multiple pharmaceutical closes and only a small selection of these is tested using the impactor. The rest are fired into a waste firing subsystem 64. When the selected number of waste doses has been fired, the device is conveyed on the transfer unit to a collection subsystem 66 and is fired into the cascade impactor 10. A recovery subsystem 67 carries out the disassembly of the cascade impactor 10 and the recovery of the material captured in it. The operation of all of these functions is automated, and the system is controlled by a means of a microprocessor based device and more specifically, in the present embodiment, a personal computer.

Each of these aspects of the system will now be described, in turn, in greater detail.

The carousel 56 carries enough devices to allow the system to run for a protracted period—e.g. overnight—without being manually restocked with devices. It consists of an "off the shelf" rotary table indexable between several positions (twelve, in the illustrated embodiment) by an electromechanical drive. At each position the carousel is shaped to receive and locate a removable cassette containing multiple devices 1. In the present embodiment ten devices can be stored in each cassette. An empty cassette is placed at one position, to provide for uploading of devices after testing. Hence the illustrated carousel can store 110 devices for testing. Cassettes are manually filled prior to their installation in the system, with access for loading/removing, the devices being through the open top of the cassette. A slot runs the length of each cassette, as seen in the drawing, to expose the devices' mouthpieces and to aid removal of the device from the cassette. The cassette contains guide rails to locate each device in the illustrated orientation, mouth outward. In use, when a cassette has been emptied the rotary table is advanced to present a fresh cassette to the device dispensing unit 60.

The device dispensing unit 60 is used to move devices from the carousel to the device transfer unit 62. It is a servo driven two axis slide arrangement movable along the Y axis (which is marked FIG. 2) to advance/retract it relative to the carousel, and along the Z axis (perpendicular to the plane of the paper, in FIG. 2) to enable it to move to the height of the chosen device (the topmost in the cassette) and to raise it to remove the device from the carousel. The device dispensing unit 60 has an end effector 70 in the form of a vacuum cup for picking arid placing the devices 1. The Z axis incorporates an optical sensor used to verity that there is a device at the chosen location, and that the device has been picked up by the end effector.

In operation, the end effector 70 is placed upon a flat of the device and a vacuum is applied to securely retain the device, which is then lifted out of the cassette and placed upon platform 68 of the device transfer unit 62.

Figure 3:
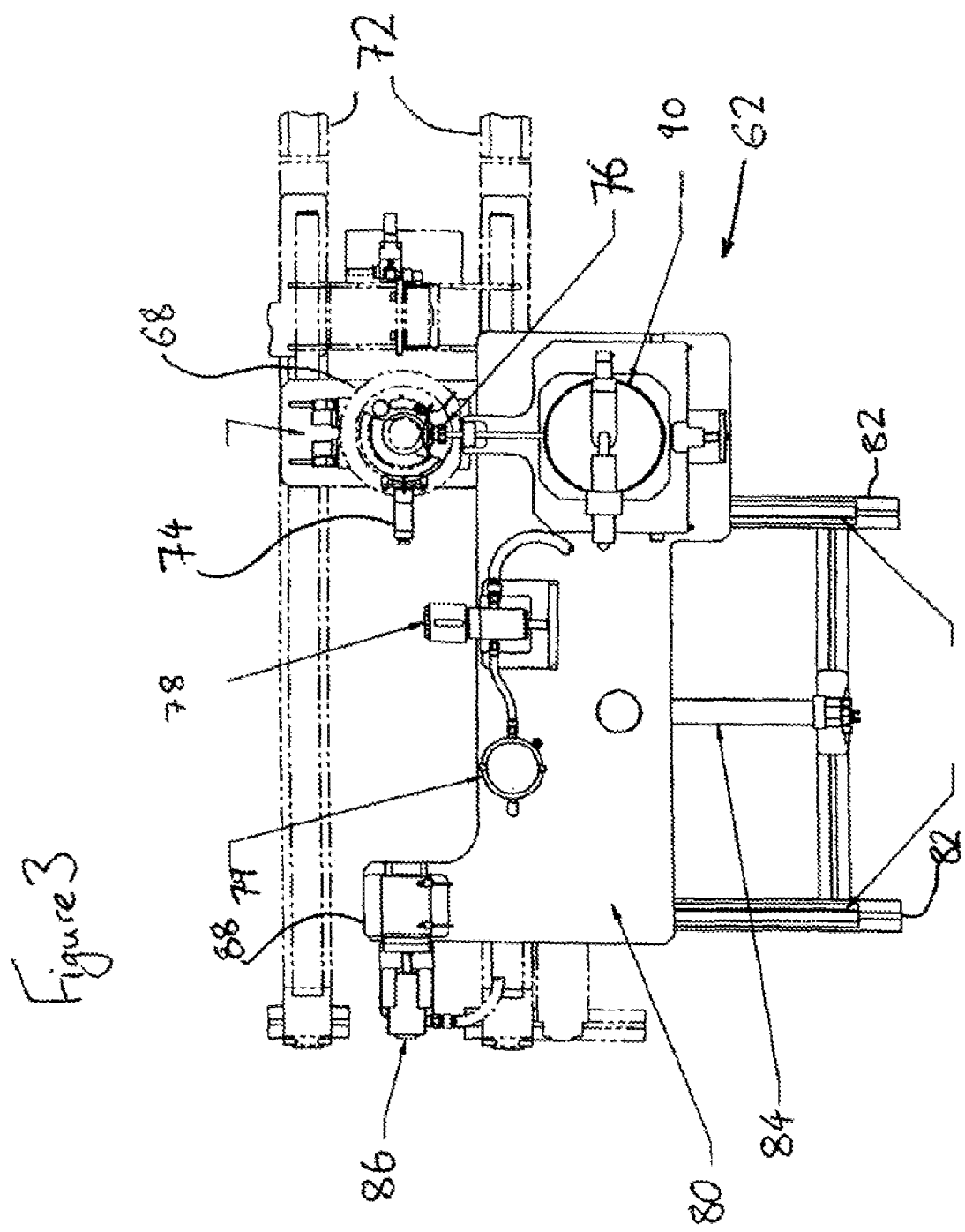
FIG. 3 is a plan view of a device transfer unit and waste firing subsystem of the system.
Figure 4:
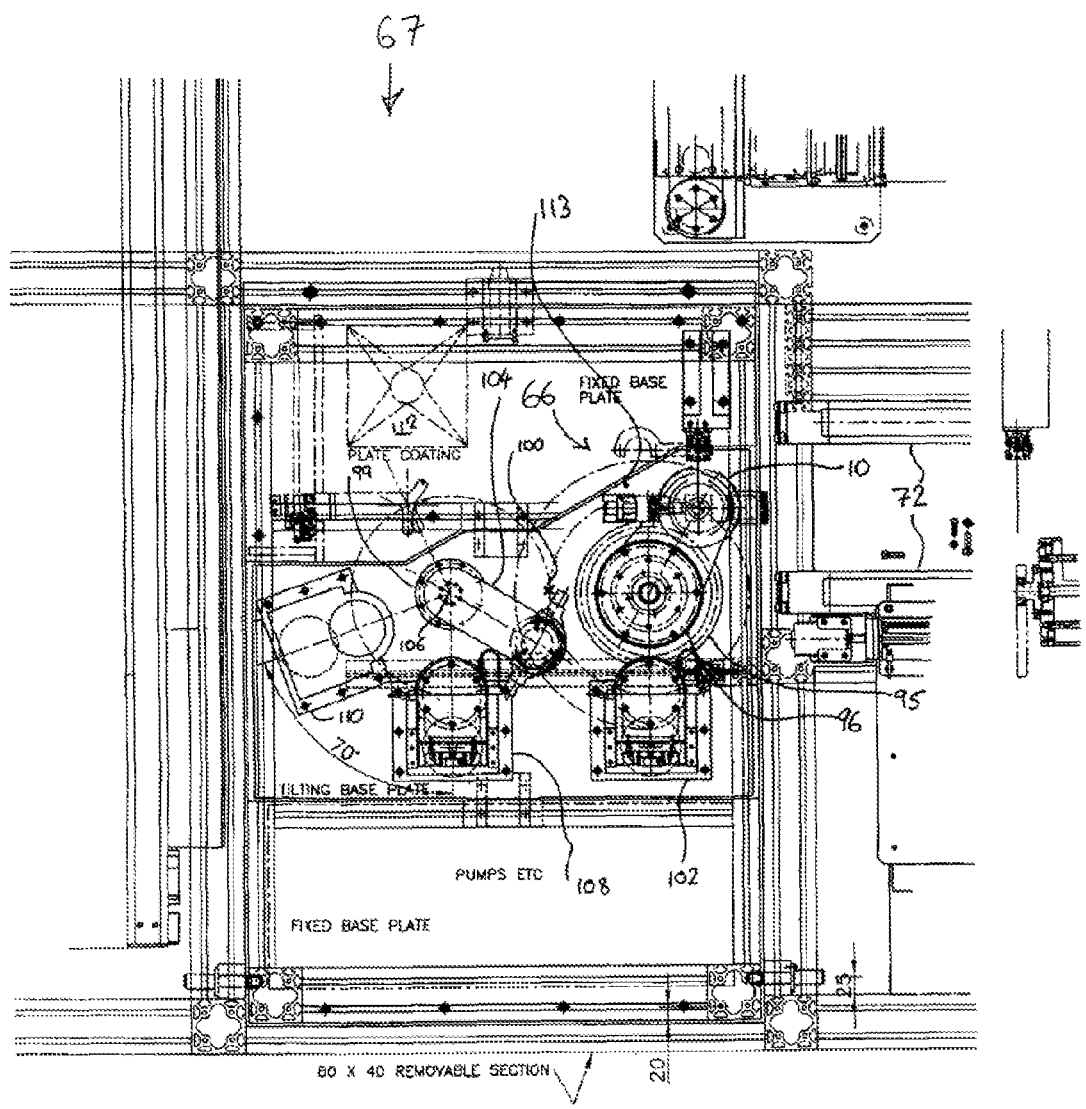
FIG. 4 is a plan view of cascade impaction and recovery subsystems.

The device transfer unit 62 is best seen in FIG. 3 arid rides on a linear slide way 72 aligned along the X-axis (whose direction is marked on the drawing). The device transfer platform 68 is movable along the linear slide way by a servo drive under software control. The device transfer unit also carries a rate testing utility mouthpiece 74, whose purpose will be explained shortly. The device transfer platform 68 incorporates a device firing mechanism. As noted above, the inhaler devices 1 have a mechanical, user operable mechanism for releasing the pharmaceutical dose to be inhaled. This mechanism can take a variety of forms, but in the illustrated devices it has a trigger lever movable about a vertical axis (i.e. an axis perpendicular to the plane of the paper, in FIG. 2) to pierce one of a set of blisters within the device 1 and release the pharmaceutical drug contained in it. The firing mechanism (not clearly seen in the drawings) comprises a firing pin to engage the trigger lever and a servo drive which moves the tiring pin through an arc to actuate it. A torque transducer is used to measure the firing torque.

The device transfer platform 68 is carried upon a rotary fable for rotating it—and the device 1 carried upon it—through 90 degrees, enabling the device mouthpiece to be presented to different subsystems. The device transfer unit is adapted to move the device between four positions:

(1) a device dispensing position, for receiving the device from the device dispensing unit 60;
(2) a waste dose collection position, in which the device mouthpiece is presented to a waste fire mouthpiece 76;
(3) an airflow resistance (AFR) position, in which the device mouthpiece is presented to an AFR mouthpiece 78; and
(4) a testing position, in which the device mouthpiece is presented to the mouthpiece 12 of the cascade impactor 10. Note that this requires the device 1 to be rotated through 90 degrees relative to the other positions, using the rotary table.

Also the device transfer unit has two further positions, to locate the utility mouthpiece 74 respectively against the waste fire mouthpiece 76 and the AFT testing position.

The servo drive of the device transfer platform 68 is controllable to selectively provide both (a) position control, which is used to move the platform to positions 1, 2, and 3 and (b) torque control (i.e. torque control of the rotary drive, or equivalently control over the linear force upon, the platform) which is used in position 4 to urge the device mouthpiece against the impactor mouthpiece 12 with a chosen force (in this embodiment 30 Newtons) to provide a leak proof seal between the mouthpieces.

To avoid excessive movement of the device 1 during firing and testing, respective releasable overhead pneumatic clamps (not seen in the drawings) are provided. These clamps urge the device against the platform 68 whilst it is in each of positions 2-4.

The components of the system seen in FIG. 3, and particularly the waste firing subsystem 64, perform the preparation of the device 1 prior to cascade impaction testing. A waste firing carriage 80 is mounted upon linear guide rails 82 for movement along the Y axis under the control of a pneumatic linear actuator 84. Upon the waste firing carriage 80 are:

(1) a device preparation utility mouthpiece 86 for interfacing with the mouthpiece 12 of the cascade impactor 10, to provide for leak and flow rate testing of the impactor. The device preparation utility mouthpiece 86 is mounted on a linear actuator 88 aligned along the X axis to enable it to be advanced into and retracted from the impactor mouthpiece 12, and incorporates a solenoid valve to enable flow rate setting, when it vents to the atmosphere, and leak testing, for which the valve is closed.

(2) the waste fire mouthpiece 76, which is positioned to interface with the mouthpiece of the device 1 and to collect waste doses from it. The waste fire mouthpiece communicates with a filter and filter chamber 90 for collecting particles in the waste doses, and via the filter chamber with a vacuum pump, which is not seen in FIG. 3.

(3) the AFR mouthpiece 78, which is again positioned to interface with the mouthpiece of the device 1 and which is communicable with the vacuum pump via a differential pressure sensor 79.

The mouthpieces 86, 76 and 78 are spring loaded, so that when the device 1 is suitably positioned the relevant mouthpiece is spring biased against it with a reproducible and adjustable sealing force.

To explain the waste dose firing process in more detail, it should first be noted that the device 1 may for example contain 14, 28 or 60 doses in respective blisters. Blister dose access is sequential. To test blisters other than the first available, waste firing is performed until the desired blister is reached. Waste doses are not required for testing and are collected by means of the filter and filter chamber 90. Air is drawn through the waste fire mouthpiece 76 during waste firing to extract the dose and prevent build up of powder on the device mouthpiece, which would otherwise potentially contaminate the test samples. The rate of air flow is tested and adjusted automatically to a user definable rate prior to each waste firing sequence, by adjustment of an analogue valve. To test the rate of air How, the waste firing carriage 80 is withdrawn, the device transfer unit 62 is moved to align the rate testing utility mouthpiece 74 with the waste fire mouthpiece 76, and the waste firing carriage is advanced to mate the two mouthpieces. Air is drawn through the mouthpieces, the flow rate being measured, and the analogue valve is adjusted under software control to achieve the desired flow rate.

Once the air flow rate has been set, waste dose collection can begin. The waste firing carriage 80 and the device transfer unit 62 are moved to mate the waste fire mouthpiece 76 with the mouthpiece of the device 1. The device 1 is locked in place by means of the aforementioned overhead pneumatic clamp and is mechanically fired to release the test dose, as described above. The vacuum pump is used to draw air through the device for a chosen period, to withdraw the waste dose. Tire fire and extract cycle is repeated until the dose required for testing is reached.

The system is also able to test the airflow resistance of the device 1. In this process the device is first fired and the dose extracted and collected as just described. The device trigger is held in the "open" position. The waste firing carriage 80 is withdrawn, the device transfer unit aligns the device mouthpiece with the AFR mouthpiece 78, and the waste firing carriage 80 is advanced to mate the device and AFR mouthpieces, creating a leak proof seal by virtue of the spring biasing of the AFR mouthpiece 78. A chosen airflow rate is drawn through the device and its resistance is measured as a differential pressure across the sensor 79.

The device preparation utility mouthpiece 86 is used for leak testing and airflow rate testing the cascade impactor 10. Leak testing involves mating the utility mouthpiece 86 with the mouthpiece 12 of the cascade impactor 10, locking the device in place with the relevant overhead clamp, and then creating a partial vacuum in the cascade impactor 10 by drawing air from it with a vacuum pump, then sealing the impactor and monitoring pressure rise over a chosen period. Airflow rate testing of the impactor is carried out prior to collection of each sample. The utility mouthpiece 86 is presented to the mouthpiece 12 of the impactor, as before. The vacuum pump is enabled and draws air through the cascade impactor 10. A calibrated mass flow meter is used to measure the airflow rate and initial and final flow rates are recorded.

The function and operation of the cascade impaction subsystem 66 will now be described, with particular reference to FIG. 4, beginning with the process of collection of a test dose in the cascade impactor 10. The mouthpiece of the device 1 is engaged with the mouthpiece 12 of the cascade impactor 10 by means of the device transfer unit 62, the device being rotated through 90 degrees by means of the rotary table as explained above, and is biased against the mouthpiece 12 with a chosen force using the transfer unit's torque control mode. The aforementioned pneumatic clamp applies force from above to the device 1 to maintain it in position. The device is then mechanically fired in the manner explained above, and a vacuum pump communicating with the conduit 24 leading from the final stage of the cascade impactor 10 (see FIG. 1) is used to draw air through the device 1 and the impactor 10 for a chosen period. Tire test dose is drawn into the cascade impactor along with the air, in tire form of an aerosol and is collected—as described above—in the throat 14, preseparator 22 and stages A-I of the impactor. A single dose may be collected in the impactor 10 in this way or, according to user requirements and under software control, two or more such doses may be collected.

The cascade impactor 10 is then automatically disassembled and the sample material collected in the throat 14, preseparator 22 and stages A-I is separately recovered automatically by solvent washing processes. This process will now be described.

The first step of disassembly is to remove the throat 14 from the cascade impactor 10 and move it to a throat recovery station 92 (FIG. 2). This is done using a manipulator comprising a five axis gantry carrying a gripper which is movable along X, Y and Z directions, and rotatable about two axes. The manipulator is not illustrated, but suitable devices are well known to those skilled in the art. The gripper is adapted to hold both the throat 14 and the preseparator 22. To release the taper 16 through which the throat 14 engages with the cascade impactor 10, the throat is rotated about the gripper's first rotational axis as it is withdrawn. An alternative would be to adapt the impactor and throat to dispense with the taper and to use instead axially lacing seals, which would not resist withdrawal of the throat. The transfer of the throat needs to be carried out in a manner which prevents material collected upon its internal surfaces from being dislodged and lost. To this end rotary motion of the gripper about its second axis (pitch) is used to turn the throat, once it is clear of the impactor, so that its elbow is lowermost and material cannot fall out of it. The throat recovery station 92 will be described below. The same manipulator is then used to disengage the preseparator 22 from the remainder of the cascade impactor 10 and transfer it to a preseparator recovery station 94, which again will be described below.

Tire recovery subsystem 67, by which the stacked stages and plates of tire cascade impactor 10 are first separated, then solvent washed to recover the test material collected upon them, men further washed to clean them and finally dried and reassembled, is seen in FIG. 2 but is shown in more detail in FIGS. 4-7. An expander device 96, seen in plan in FIG. 4 and in side views in FIGS. 5*a* and 5*b*, is used to expand the stages A-I of the cascade impactor—i.e. to move each stage vertically apart from its neighbours above and below. The expander device sits upon a rotary table 95 having an axis 97 and is rotatable to place the cascade impactor 10 in three different positions—a collection position, in which it is indicated in phantom at 98 in FIG. 4; a plate removal position indicated by a cross 100 in the same drawing; and a stage recovery position defined by a stage recovery station 102. The impaction plates 46 A-I are handled by a stack of plate-handling arms 104, one of which is illustrated in FIGS. 6*a*-*c*, and which are mounted on a further rotary table 99 whose axis is indicated at 106. Rotation of this rotary table permits the plates to be moved between four positions—the plate removal position 100; a plate recovery position defined by a plate recovery station 108; a plate storage location defined by a plate storage station 110 and a plate coating position defined by a plate coating station 112. The stage and plate recovery stations 102, 108, and also the expander device 96 and the plate-handling arms 104, are all mounted upon a tilting base plate 113 winch enables them to be inclined, under software control, about a horizontal axis, for reasons which will be explained below.

In FIG. 5*a* the cascade impactor 10 is shown assembled. In FIG. 5*b*, the expander device 96 has been used to expand—i.e.

to disassemble—the stages A-I of the impactor. The expander device 96 has an upright, threaded lead screw 114 which lies along the device's rotational axis 97 and is rotatably mounted toward its lower end through rotary bearings 116 in a boss 118 of an expander base plate 120, and toward its upper end through a rotary bearing 122 in an expander top plate 124. The base 40 of the cascade impactor 10 is fixed to the expander base plate 120. A top plate boss 126 projects from the top plate into a further rotary bearing 130 to locate the top plate while allowing it to rotate along with the rest of the expander device upon its rotary table. The lead screw 114 is driven by an electric motor 132 suspended beneath the expander base plate 120. Extending between and bolted to the expander top plate 124 and the expander base plate 120, lying parallel to the lead screw 114 and on opposite sides of it, are front and rear guide rods 134, 136. For each stage A-I of the impactor 10 (and there are nine of them in the present embodiment) there is provided a respective expander arm 138A-I. Each expander arm has three through-going apertures which respectively receive the lead screw 114 and the front and rear guide rods 134, 136. Each expander arm has a single flanged bush 140 which is a sliding fit upon one of the guide rods 134, 136, and the locations of the bushes alternate. That is to say, one arm has a bush 140 which rides upon the front guide rod 134, and the next has a bush which rides upon the rear guide rod 136. Each bush 140 projects beneath its expander arm 138 as seen at 142, so that in the assembled state (FIG. 5a) each projects into the aligned aperture in the next arm down. The topmost expander arm 138A is linked through a pin 144 to a suspension boss 146 which is threadedly received upon the lead screw 114. Tire suspension boss is prevented from rotating by the pin 144 so that rotating the lead screw causes it to move up or down. The pin 144 is screwed into the expander arm 138A and passes upward from it through a flange of the suspension boss, terminating in an enlarged head above the said flange. In the assembled state (FIG. 5a) there is some clearance between the head and the top surface of the flange, so that the suspension boss 146 moves a short distance before it begins to raise the expander arm 138A. Further pins of generally similar type, but greater length, link the topmost expander arm 138A to the arm 138B beneath, and each successive pair of arms below that. The pins are circumferentially staggered so that they do not foul each other, and consequently lie outside the plane of the drawing and are not seen. As the lead screw is driven to raise the suspension boss 146, successive expander arms 138A-I are suspended from the arm above and so raised, so that when the boss 146 is at the upper end of its travel all of the arms are vertically separated, as seen in FIG. 5b, Each expander arm 138 projects forwardly beyond the front guide rod 134 to receive and embrace a respective impactor stage body 301. Hence in the expanded state the stage bodies are themselves expanded, and access is enabled to the impaction plates 46A-I resting upon them. Note that the stage fillers 42 are fixed to the stage bodies 30.

The expanded stages of the cascade impactor 10 are moved to the plate removal position 100 by turning the rotary table 95 supporting the expander device 96. The plate-handling arras 104 are then moved to the same position and used to remove the impaction plates 46 from the impactor stages. FIGS. 6a-c show only a single plate-handling arm 104, but the system has an arm for each impactor stage, the arms being positioned one above another to align with the stages in the expanded impactor. Each has a radially extending cantilevered arm member 148 having a fixed inner end 150 and carrying at its opposite end a pneumatic engagement device 152 for picking and placing the impaction plate (which is omitted from these drawings). The device comprises an opposed pair of linear pneumatic actuators 154, 156 having downwardly projecting claws 158, 160 which are movable toward and away from each other. The actuators 154, 156 are vertically movable relative to the arm member 148 by means of a pneumatic bellows arrangement 158 which also carries downwardly projecting locating features 160. To grasp the impaction plate, the bellows arrangement is used to lower the actuators 154, 156 so that the locating features rest upon the plate, defining the required vertical position, and the claws 158, 160 are then advanced to engage the plate. This is done concurrently by each of the plate-handling arms 104, to engage each of the impaction plates 46A-I.

The impaction plates 46 and the stage bodies 30 are then conveyed to their respective recovery stations 102, 108. The stage recovery station 108 is best seen in FIGS. 7a-d. The stage bodies are moved to it by rotating the expander device 96 using its rotary table 95. The stage recovery station 102 has an upright beam, referred to as a strongback 162, supporting respective stage recovery devices 164 for each of the impactor's stage bodies 30. In the present embodiment there are thus nine stage recovery devices 164A-I, arranged one above the other. Each comprises a fixed arm 166 carried upon the strongback 162 and a vertically movable arm 168 carried upon a vertically extending slider 170 which is slidably coupled to the strongback 162 to enable it to move up and down. A stage recovery lead screw 172 driven by an electric motor 174 threadedly engages a slider boss 176 to control vertical motion of the slider 170. Each movable arm 168 carries a downwardly facing upper space saver 178 having a circular boss 180 surrounded by an upper sealing rim 182. Each upper space saver 178 is bolted to the underside of its movable arm 168 at 184, 186, and is separated from it by springs 188, 190, allowing it to move upwardly somewhat against the springs. Each fixed arm 166 carries an upwardly facing lower space saver 192 shaped to provide a shallow frusto-conical portion 194 surrounded by a lower sealing rim 196. Limited vertical motion of the lower space saver is provided for by mounting it upon a pneumatic bellows arrangement 196.

In use, the impactor stage bodies 30, still carried in the expander arms 138, are positioned between the respective upper and lower space savers 178, 192. The stage recovery lead screw 172 is driven to bring the upper space savers 178 downward until their sealing rims 182 engage the upper surfaces of the stage bodies 30, the springs 188, 190 urging them into engagement therewith. The bellows 196 are pressurized to raise the lower space savers 192, bringing their sealing rims 196 into contact with the lower surfaces of the stage bodies. The interior of each stage body 30A-I is thus placed in a closed chamber into which solvent etc. can be introduced through respective supply passages 200. Note that because the spaces savers 178, 192 fill most of the interior space of the stage bodies, the volume of solvent needed to Hood the chambers is minimized.

After recovery of the test material by solvent washing, and cleaning and drying of the stage bodies 30 (which processes will be described below) the stage bodies 30 are released and returned to the plate removal position 100 for replacement of the impaction plates 46.

The plate recovery station 108 is best seen in FIGS. 8a-d. Like the stage recovery station it has an upright strongback 202 carrying a respective plate recovery device 204A-I for each of the impaction plates. Each plate recovery device comprises a fixed arm 206 carried upon the strongback 202 and a movable arm 208 carried upon a slider 210 which is movable along the strongback by means of a lead screw 212 driven by a motor 214 and threadedly engaging with a slider boss 216 mounted on the slider. A respective lower receptacle plate 218 carried on each of the fixed arms 206 has a shallow circular depression 219 in its upper surface to receive the impaction plate. A respective upper receptacle plate 220 suspended from each movable arm through bolts 222, 224 and separated from it by springs 226, 228 disposed around the bolts has a complementary shallow depression 221 in its lower face, hi use, the impaction plates 46 are placed in the depressions in the lower receptacle plates 218 by means of their respective plate-handling arms 104, and are then released from the arms which are moved to a safe position, then the upper receptacle plates 220 are brought down into contact with the lower receptacle plates. Each impaction plate is thus contained in a respective closed receptacle defined by the depressions 219, 221. The springs 226, 228 urge the receptacle plates together to maintain a seal. Solvent washing etc. is performed, then the upper receptacle plates are raised and the plate-handling arms are used to pick up the impaction plates 46 and move them to the next station.

Recall that the stage and plate recovery stations 102, 108, and associated components, are supported on a tilting base plate 113. The reason for this is to assist liquid removal from the recovery chambers formed around the stages and plates, these chambers being flat bottomed, so that while the chambers are liquid tends to spread across the entire chamber floor, making effective collection difficult. For liquid removal plate 113 is inclined—say at 45 degrees—so that liquid collects in the lowermost extremity of each chamber. The outlet from each such chamber is disposed in this lowermost extremity, making liquid removal more effective.

Processing of the impaction plates 46 is slower than processing of the stage bodies 30 because the former undergo a coating step, to be explained shortly. However plate recovery and plate coating can be carried out simultaneously, and to avoid the plate processing limiting the speed of the whole operation, two sets of plates are used. When necessary, one set of impaction plates 46 is placed upon the plate storage station 110 using the plate-handling arms 104 whilst the other set is moved using the arms.

After recovery of the test material from the impaction plates 46, they are moved using the plate-handling arms 104 to the plate coating station 112. As mentioned above, some impaction tests require the impaction plates 46 to be precoated with a material such as silicone, to improve particle adhesion. The plate coating station, best seen in FIGS. 9a-d, comprises an upright rear panel 230 carrying a respective plate support arrangement 232 for each of the impaction plates 46, these arrangements being one above another to correspond with the heights of the plate-handling aims 104. Each comprises a horizontal guideway 234 slidably supporting a travelling support 236 movable along the guideway under software control and carrying a support plate 238 for receiving the impaction plate 46. A spray platform 240 supports a spray head 242 and is movable vertically along the rear panel 230 to bring the spray head to the level of each plate support arrangement 232 in turn. The relevant travelling support is then moved to pass its impaction plate 46 through the spray from the head 242 and cause it to be coated. After coating of all the impaction plates 46 they are returned to the stage bodies 30 for re-assembly of the cascade impactor 10.

An alternative form, of the recovery subsystem 67 is schematically depicted in FIGS. 10-19. Whereas in the version described above the impaction plates 46 and stage bodies 30 are all moved from station to station together, the FIG. 9 version serves to split them into two sets (referred to as even and odd sets) which are separately, but concurrently, processed in respective stations.

Figure 10:
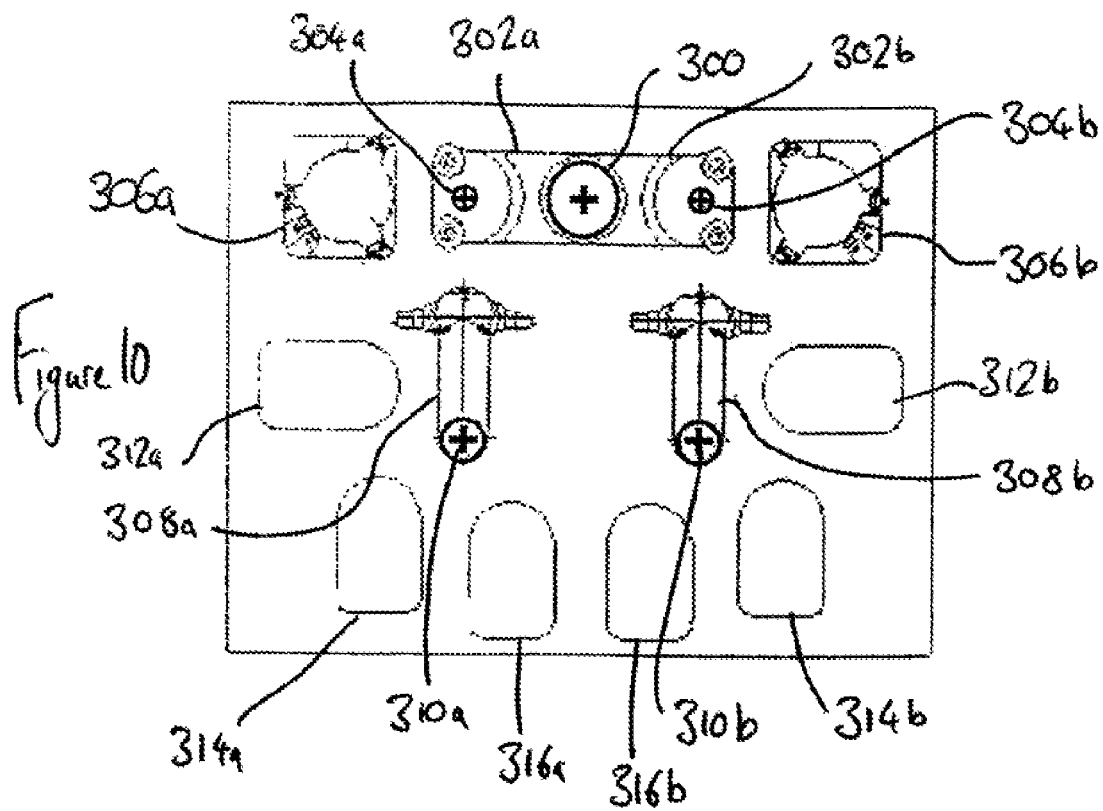

In FIG. 10 an expander device 300 is formed similarly to the expander device 96 already described, but has two sets of expander arms 302a,b which pivot about separate axes 304a,b and serve to carry the even and odd impactor stages respectively. Even and odd stage recovery stations 306a,b are positioned in reach of the expander arms 302a,b. Even and odd plate-handling arms 308a,h rotatable about axes 310a,b are positioned to receive the impaction plates 46 from the expander arms 302a,b and to move the impaction plates between:

(1) even and odd plate recovery stations 312a,b
(2) even and odd first set plate coating stations 314a,b and
(3) even and odd second set plate coating stations 316a,b.

Figure 11:
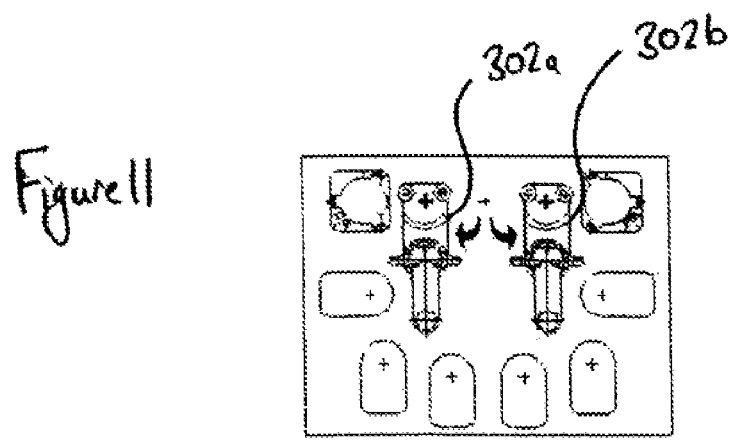
Figure 12:
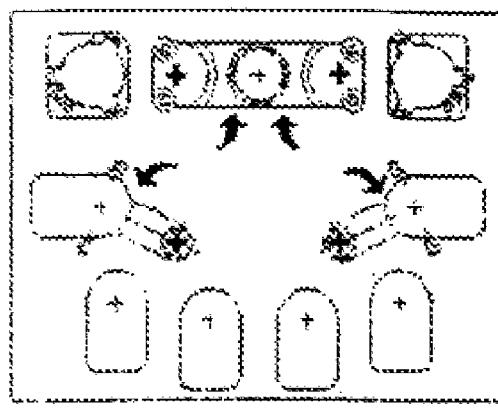

The sequence of operations is as follows. The stages bodies 30 (FIG. 1), and the impaction plates 46 supported upon them, are expanded, then the even and odd stages are simultaneously moved ninety degrees on their respective expander arms 302a,b, the even stages moving clockwise and the odd stages anticlockwise, to their plate removal positions (FIG. 11). The impaction plates 46 are picked up by the plate-handling arms 308a,b and moved to their respective recovery stations 312a,b (FIG. 12).

Figure 13:
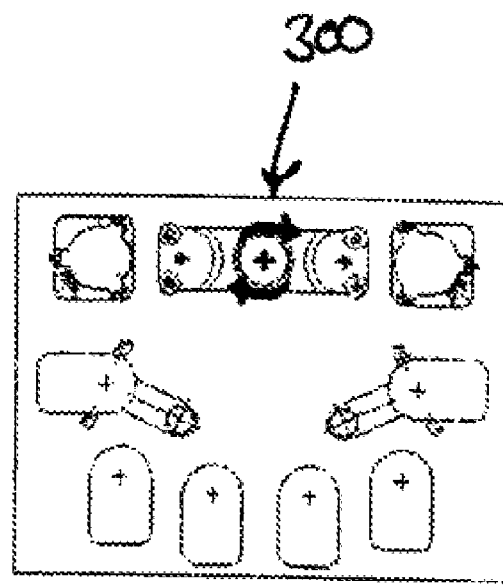
Figure 16:
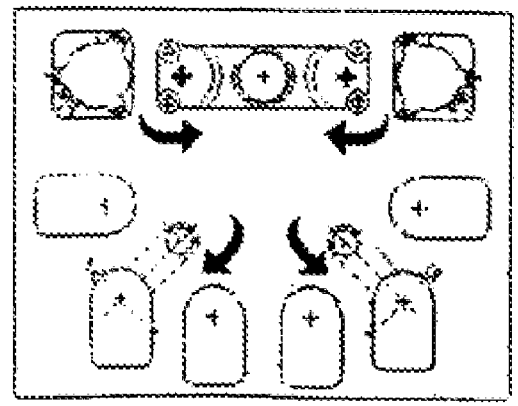
Figure 17:
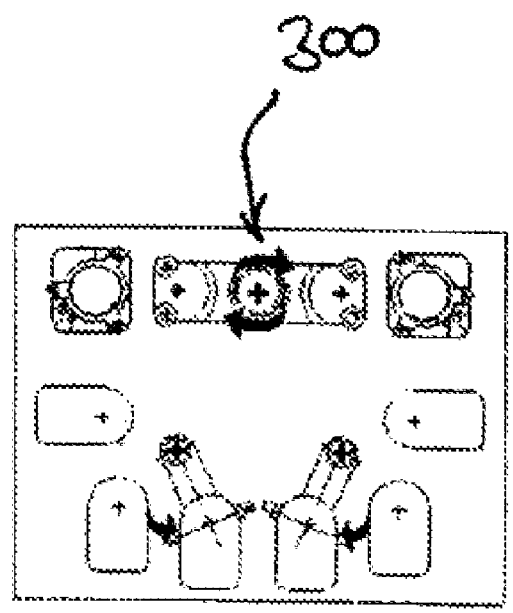
Figure 18:
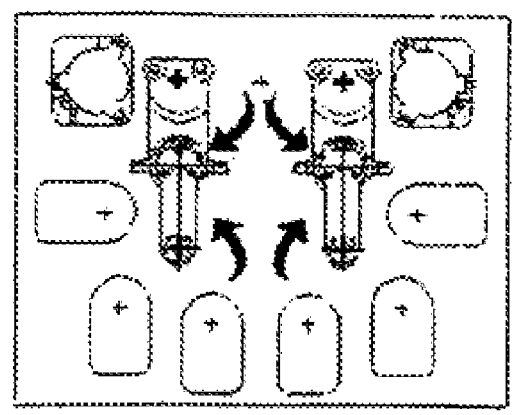

Note that at this point the even stage bodies 30 are on the same side of the apparatus as the odd impaction plates 46, since odd plates rest upon even bodies. To associate even stage bodies with even impaction plates and odd stage bodies with odd impaction plates, the whole expander device 300 is turned through 180 degrees on a rotary turntable (FIG. 13). This assists in subsequently correctly combining assays from the stages and impaction plates. The plate-handling arms 308a,b are moved to safe positions (FIG. 14) and the even and odd expander arms 302a,b are moved through 180 degrees, in opposite directions, to present the stage bodies 30 to their recovery stations, where recovery of test material, washing and drying are carried out (FIG. 15).

The provision of two pairs of plate coating stations 314a,b and 316a,b enables two sets of impaction plates 46 to be used. After undergoing recovery, washing and diving at its recovery station, one set of impaction plates is moved to its coating station by means of the plate-handling arms 308a,b, then the other set, already coated and located in the other pair of coating stations, is picked up with the same arms. The coating stations in this embodiment.

Figure 19:
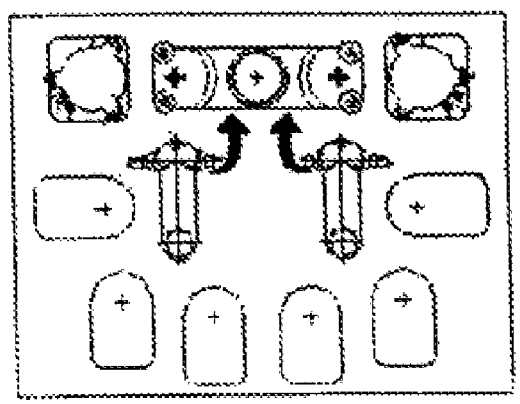

Re-assembly of the cascade impactor involves moving the stage bodies 30 back to the central assembly location (FIG. 16), rotating the expander device 300 through 180 degrees to return it to its original position (FIG. 17), returning the plates to the stage bodies (FIG. 18) and again moving tire stage bodies—now carrying the impaction plates—back to the central assembly location so that the impactor stages can be brought back together using the expander device (FIG. 19).

Figure 20:
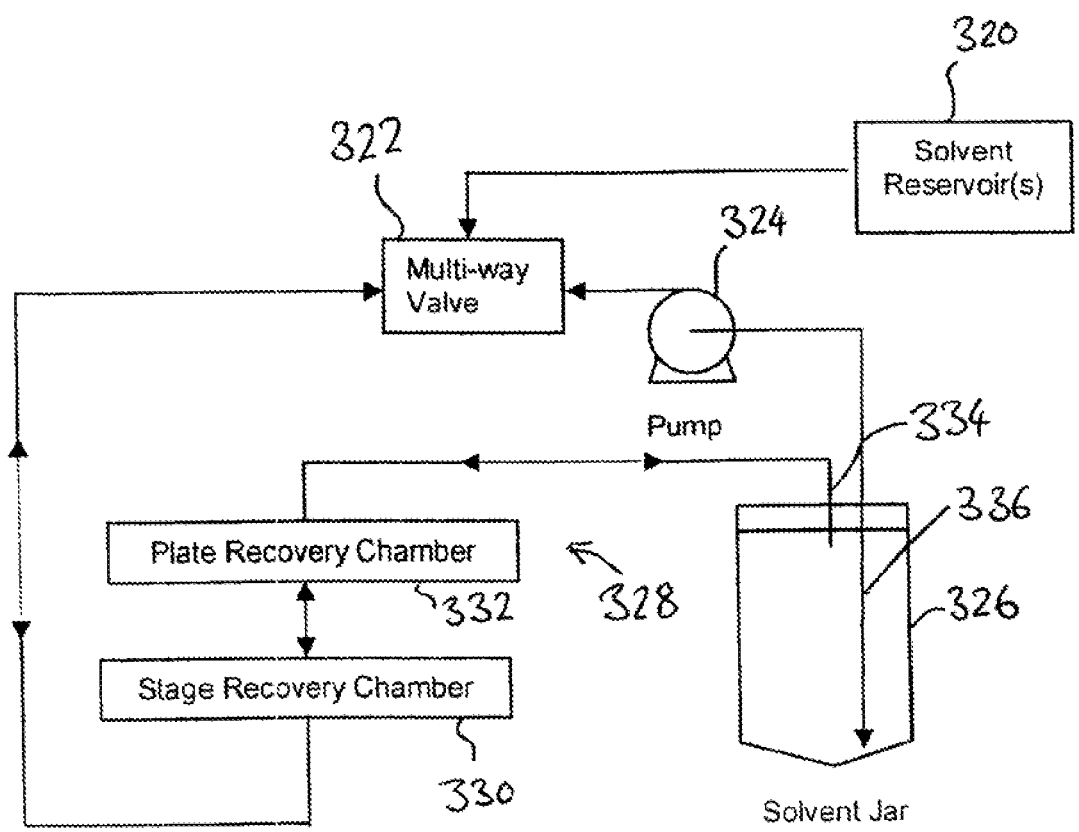
FIG. 20 is a schematic representation of a fluid circuit used in the recovery subsystem.

FIG. 20 is a schematic representation of one of a set of fluid circuits used for the recovery process itself during which the test material collected upon each impactor stage A-I is dissolved in a known quantity of solvent. The apparatus incorporates bulk solvent containers, one of which is represented at 320. Solvents to be used may include methanol, acetonitrile and water. A multi-way valve 322 is arranged to place the chosen solvent container 320 in communication with a metered pump 324. This is a displacement type pump which is able to supply a specified liquid volume, determined by the software. The pump used in the prototype system is accurate to 0.5%. The pump 324 draws a chosen volume of solvent into a reservoir 326, and the multi-way valve 322 is then switched to close a fluid circuit 328 for circulation of the solvent. The circuit includes a stage body recovery chamber, schematically represented in this drawing at 330, and the recovery chamber 332 for the corresponding impaction plate, as well as the pump 324 and the reservoir 326. The pump circulates solvent through this loop for a chosen period, which aids dissolution of the test material in solvent and ensures that the solution produced is homogeneous. At the end of this circulation, reversal of the pump ensures that all of the solution is returned to the reservoir 326. Note that although the reservoir has two ports 334, 336 only one—which serves as the outlet during circulation—reaches the fluid level in the reservoir, so that when the pump is reversed no fluid is removed from the reservoir. The tilting, plate 113 is inclined, as explained above, to facilitate withdrawal of liquid from the recovery chamber. The solution thus collected in the reservoir 326 is representative of the material collected in the relevant stage of the cascade impactor 10.

This recovery process is carried out in parallel for all impactor stages A-I, and for the throat 14 and preseparator 22. Depending upon user requirements, the required connections may be simplified somewhat by grouping—and connecting—stages together, so that the resultant assay will contain material from multiple stages. Similarly the throat 14 and preseparator 22 may be connected together during recovery to provide a single common assay.

Some test materials may require more than one solvent for recovery, and in this case the process can be repeated using a chosen dose of the second solvent, and a loop containing a second reservoir, although typically the two assays will then be combined. The solution is then ready for bulking or sampling, which will be described shortly.

The various components seen in FIG. 20, and the impactor parts contained in the chambers 330 and 332, then need to be cleaned, particularly to prevent contamination of one sample by its predecessor. This is done by circulating solvent through the circuit and then pumping it to a waste container. The impactor components then need to be dried. This may be achieved using forced airflow. The recovery units would be opened and subject to localized air extraction to promote solvent evaporation. Alternatively atmospheric drying may be sufficiently rapid, depending on the volatility of the solvent selected. Another option is to use a highly volatile solvent for the final wash, which will quickly evaporate off the impactor components. The solvent lines do not need to be dried, but are primed with solvent ready for the next cycle.

The term "bulking" used above refers to the process of combining two or more recovered solutions in a single assay. Using the multi-way valve 322, the pump 324 is connected to a chosen reservoir 326 and a small volume of the solution contained in it is pumped to waste to prime the lines. A metered quantity of the solution is then dispensed into a bulking pot. The process is repeated with one of more further solutions. Mixing is carried out by circulating the combined solutions in a closed loop.

Any suitable method may be used for analysis of the solutions. In practice, analysis typically involves some form of chromatography, such as high pressure liquid chromatography (HPLC), an optical technique which is well known, in principle, such analysis could be carried out on a continuous basis by passing the bulked solutions through "in line" chromatographic devices. More typically, a separate automatic chromatography machine will be used and the solutions will be passed to that machine in vials. Hence the product of a protracted run of the present system will be a large of solution-containing vials, which are stored in a rack and are place-encoded. That is, the position of the vial in the rack represents its content. Solutions are transferred from the reservoirs 326 to the vials (not shown) by a vialling unit, which is not shown but is of well known type. A suitable unit is a two axis device with multiple sampling needles or tips, the reservoirs being arranged so that the selected tips can all be simultaneously introduced to respective reservoirs, after which solution is drawn into each. The tips are moved to the vial rack and inserted through self sealing septum type vial lids, then a metered dose of each solution is discharged into the respective vial. Spaces may be left in the vial racks for calibrations and standards, to be inserted manually.

The system as a whole will typically be enclosed in a housing provided with air extraction, since some of the solvents used are both volatile and explosive, and with interlock protection against inappropriate user access.

What is claimed:

1. An expander device for expanding and a cascade impactor of the type comprising multiple impactor stages each comprising a respective stage body, the stage bodies being shaped to enable them to be assembled in a stack, locating one upon another, to form a conduit for through-flow of an aerosol sample, the stack having an axis, the expander device comprising a respective arm member for supporting each stage body, an arrangement for supporting the arm members such that they are movable along the direction of the said axis, and a mechanism for moving the arm members away from each other along the direction of the said axis to expand the impactor stages, and for moving them together along the direction of the said axis to re-assemble the impactor stages.

2. An expander device as claimed in claim 1 in which the arm members are slidably supported on at least one elongate guide member extending in the direction of the said axis.

3. An expander device as claimed in claim 1 comprising a lead screw, a rotary lead screw drive, and at least one boss which engages the lead screw so as to be moved along the lead screw by rotation of it.

4. An expander device as claimed in claim 1, which is adapted to receive the impactor with its axis at least substantially upright, at least some of the arm members having an extensible coupling to their neighbouring arm member, the extensible coupling being constructed to accommodate some relative motion of the neighbouring arm members but to prevent them from moving apart more than a maximum distance, so that raising the top-most arm member causes arm members beneath it to be suspended from it through the extensible couplings, and thereby to be separated from each other.

5. An expander device as claimed in claim 4 in which the extensible coupling comprises an elongate coupling member which is coupled to one arm member and is movably received by the other, the elongate coupling member having a stop feature which limits its movement relative to the said other arm member to define the said maximum distance.

6. An expander device as claimed in claim 5 in which the elongate coupling member is a pin with an enlarged head received in a bore in the said other arm member.

7. An expander device as claimed in claim 1 which is mounted for rotation about the said axis, or about an axis substantially parallel to the said axis, the stage bodies being offset from the rotational axis so that by rotary movement of the device the stage bodies are movable from one processing station to another.

8. An expander device as claimed in claim 1 which further comprises a support platform for supporting the assembled impactor from beneath, the support platform being provided with a conduit connectable to a vacuum source to cause the aerosol to be drawn through the impactor.

9. A recovery device for recovering material collected upon working surfaces of components of a cascade impactor of the type comprising multiple impactor stages each comprising a respective stage body, the stage bodies being shaped to enable them to be assembled in a stack, locating one upon another, to form a conduit for through-flow of an aerosol sample, the stack having an axis, and the recovery device comprising multiple recovery stages separated vertically one from another and each adapted to receive a component from a respective impactor stage, each station comprising relatively movable upper and lower receptacle parts each shaped to receive the impactor component between themselves and having peripheral sealing surfaces, the device further comprising a drive mechanism for moving the upper and lower parts apart, so that the impactor components are able to be introduced between them along a lateral direction, and for subsequently moving the upper and lower receptacle parts together, causing the peripheral sealing surfaces to seat upon each other or upon the impactor parts, so that each recovery stage forms a closed recovery chamber containing its impactor part, the recovery device further comprising conduits for circulating liquid through each of the recovery chambers.

10. A recovery device as claimed in claim 9, in which each recovery chamber is connectable to a closed loop incorporating a pump for re-circulating liquid through the recovery chamber in any direction to promote dissolution in the liquid of material collected upon the said working surfaces.

11. A recovery device as claimed in claim 10 comprising multiple closed loops each incorporating at least one recovery chamber.

12. A recovery device as claimed in claim 11, further comprising means for dispensing a controlled dose of liquid into the closed loop.

13. A recovery device as claimed in claim 9, further comprising a valve arrangement for diverting the liquid from the closed loop to a collection vessel.

14. A recovery device as claimed in claim 9 mounted on a power driven tilting platform to enable it to be inclined to cause liquid in the recovery chambers to flow toward fluid outlets from the recovery chambers.

15. A recovery device as claimed in claim 9 in which at least one of the upper and lower receptacle parts is spring mounted, so that when the upper and lower receptacle parts are brought together the spring mounting(s) bias them toward each other.

16. A recovery device as claimed in claim 9 in which the recovery stages are separated along the direction of relative motion of the upper and lower receptacle parts.

17. A recovery device as claimed in claim 9 comprising a movable support member which carries either the upper or the lower receptacle parts.

18. A recovery device as claimed in claim 17 in which the support member is movable by means of a vertical drive.

19. A recovery device as claimed in claim 9 which is for use with hollow cylindrical impactor stage bodies, in which at least one of the upper and lower receptacle members has a space saver projection surrounded by the peripheral sealing surface, the projection being insertable into the impactor stage body by the relative motion of the upper and lower receptacle parts.

20. A recovery device as claimed in claim 9 in which both the upper and lower receptacle parts are provided with actuators for causing them to move toward/away from each other.

21. A recovery device as claimed in claim 20 in which actuator associated with at least one of the upper and lower parts is pneumatic.

22. A system for automatic recovery of test material from a cascade impactor of the type comprising multiple impactor stages each comprising a respective stage body, the stage bodies being shaped to enable them to be assembled in a stack, locating one upon another, to form a conduit for through-flow of an aerosol sample, the stack having an axis, and the system comprising:
   an expander device for separating the impactor stages from one another along the axial direction and supporting them in the resulting expanded configuration,
   at least one recovery station having multiple recovery stages separated along the axial direction for receiving respective components of the impactor stages,
   means for concurrently moving multiple components of the expanded impactor stages to the recovery station.

23. A system as claimed in claim 22 in which the expander device is mounted for rotation and provided with a powered drive, enabling it to move the impactor stages along a circular path to and from a recovery station.

24. A system as claimed in claim 22 for use with a cascade impactor of the type in which the impactor stages have respective impaction plates supportable upon respective impactor stage bodies, the aforementioned recovery station being a stage body recovery station for recovering material collected on the stage bodies and the system further comprising a plate recovery station and a plate handling device comprising multiple plate handling arms separated from each other along the axial direction, each plate handling arm having means for engaging a respective impaction plate, the plate handling device thus being adapted to engage multiple impaction plates and to move them concurrently to the plate recovery station.

25. A system as claimed in claim 24 in which the plate handling arms are commonly mounted upon a rotary platform provided with a powered drive.

26. A system as claimed in claim 24 which further comprises a plate coating station for applying a coating to the impaction plates.

27. A system as claimed in claim 26 in which the plate coating station has multiple supports for receiving multiple impaction plates, the supports being separated along the axial direction.

28. A system as claimed in claim 27 in which the plate coating station is arranged to receive the plates from the plate handling device.

29. A system as claimed in claim 26 in which the plate coating station comprises at least one spray head for spray coating the impaction plates.

30. A system as claimed in claim 22, further comprising a firing arrangement for firing a dispensing device into the impactor, the firing arrangement comprising an automated mechanical arrangement for presenting the dispensing device to a mouthpiece of the cascade impactor, a pump for providing a partial vacuum, and an arrangement of valves and conduits for connecting the pump to an outlet of the cascade impactor to cause air to be drawn through the impactor and the device.

31. A system as claimed in claim 30 which further comprises an automated mechanism for actuating a trigger arrangement of the dispensing device, to release a pharmaceutical dose from it.

32. A system as claimed in claim 30 which further comprises a store for multiple dispensing devices, a movable platform for carrying a dispensing device, and an automated manipulation arrangement for collecting a dispensing device from the store and locating it at the platform.

33. A system as claimed in claim 32 in which the store comprises a carousel with multiple device-receiving locations at intervals around its periphery, so that by rotating the carousel different device-receiving locations are made available to the automated manipulation arrangement.

34. A system as claimed in claim 32 which comprises a waste firing station for firing unwanted doses from the dispensing device, the said platform being arranged to move the device between the waste firing station and the firing arrangement.

35. A system as claimed in claim 22 which further comprises a throat recovery station and a handling system for removing a throat from the cascade impactor and conveying it to the throat recovery station.

36. A system as claimed in claim 35 which further comprises a preseparator recovery station, the handling system being suitable for removing a preseparator from the cascade impactor and conveying it to the preseparator recovery station.

37. A system as claimed in claim 22 in which the or each recovery station defines multiple recovery chambers and each recovery chamber is connectable to a closed fluid circuit comprising a fluid reservoir, a pumping device and one or more recovery chambers, enabling fluid to be circulated around the closed loop, via the reservoir and recovery chamber(s), to cause collected material to pass into the liquid and be homogenised.

38. A system as claimed in claim 37, further comprising an arrangement for supplying a controlled quantity of liquid to the closed circuit.

39. A system as claimed in claim 38 in which the arrangement for supplying a controlled quantity comprises a metered displacement type pump.

40. A system as claimed in claim 38 in which the reservoir has an inlet and an outlet, the inlet being higher than the outlet and being above a level to which the reservoir if filled, and the pumping device and/or associated valves being controllable to circulate the liquid around the closed loop in a forward direction for material collection and homogenisation, the liquid passing into the reservoir through the inlet and out through the outlet, and in a reverse direction for discharge of the liquid, causing liquid to be withdrawn from the outlet without being drawn in through the inlet.

* * * * *